United States Patent [19]
Lee et al.

[11] Patent Number: 5,453,279
[45] Date of Patent: Sep. 26, 1995

[54] ENHANCING TRANSDERMAL ABSORPTION COMPOSITIONS; TRANSDERMAL DOSAGE FORM; AND PROCESS

[75] Inventors: Chia-Shun Lee, East Brunswick; Jhili Wu; Chinhwa Cheng, both of Piscataway, all of N.J.; Chin-Chih Chiang, West Covina, Calif.; Wenchin Tsai, Piscataway, N.J.

[73] Assignee: TBS Laboratories, Inc., Piscataway, N.J.

[21] Appl. No.: 871,933

[22] Filed: Apr. 21, 1992

[51] Int. Cl.$^6$ ...................................... A61F 13/00
[52] U.S. Cl. ..................... 424/448; 424/449; 514/944; 514/946
[58] Field of Search .................. 424/448, 449; 514/946, 944

[56] References Cited

U.S. PATENT DOCUMENTS

| | | | |
|---|---|---|---|
| 4,814,173 | 3/1989 | Song et al. | 424/449 |
| 4,908,389 | 3/1990 | Mahjour et al. | 514/946 |
| 4,973,468 | 11/1990 | Chiang et al. | 424/449 |

Primary Examiner—D. Gabrielle Phelan

[57] ABSTRACT

Provided are enhancing transdermal absorption compositions useful in transdermal absorption of progestins including progesterone and optionally an estrogen for contraceptive or hormone replacement and dosage forms using the novel enhancing compositions. The enhancing compositions comprise a combination of a lower alkyl ester of a polycarboxylic acid, an aliphatic monohydroxy alcohol and an aliphatic diol. Also provided are processes of administration of progestins and optionally estrogens using the novel dosage forms.

21 Claims, 7 Drawing Sheets

SATD. PROGESTERONE IN
▲—▲ DEC:PG = 1:1
○—○ DEC:LAlc = 1:1
●—● PG:LAlc = 1:1
△—△ DEC:PG:LAlc = 1:1:1

ENHANCING TRANSDERMAL ABSORPTION COMPOSITIONS; TRANSDERMAL DOSAGE FORM; AND PROCESS

TECHNICAL FIELD

This invention relates to a novel composition useful in enhancing transdermal absorption administration of one or more progestins (for example, progesterone, levonorgestrel, norethindrone, or norethindrone acetate) and optionally with an estrogen steroid for contraceptive use or hormone replacement. Also provided by this invention are a method of administration of one or more progestins (for example, progesterone, levonorgestrel, norethindrone or norethindrone acetate) optionally with an estrogen steroid by use of dosage forms made using the composition and the dosage forms for contraceptive use or hormone replacement.

BACKGROUND ART

Progesterone is a naturally occurring progestin-type hormonal steroid. It has certain unique properties and provides unique pharmacological activities when administered. Progesterone provides certain advantages based on being a naturally occurring compound. It is useful to alleviate postmenopausal symptoms. Administration of combinations of progesterone or a synthetic progestin and an estrogen can be useful either as a contraceptive or as a hormone replacement.

It is desired to administer progesterone by transdermal absorption. Transdermal absorption provides a several hour period of administration of pharmaceuticals such as hormonal steroids often simulating intravenous administration without the problems, inconveniences and discomforts of intravenous administration. Additionally, among other reasons and advantages, transdermally administered pharmaceuticals are not subject to the problems of orally administered pharmaceuticals, which are subject to breakdown or chemical alteration by being subject to the conditions and agents present in the gastrointestinal tract.

A problem regarding administration of progesterone is the relatively large daily dosage required, for example, 10 to 30 mg.

Synthetic progestins can be used instead of progesterone, for example, levonorgestrel, norethindrone, norethindrone acetate, and the like.

It is therefore desired to provide steroid transdermal dosage forms and compositions which are useful in making those forms which result in enhancement of the rate of progesterone or other progestin absorption either alone or in combination with other hormonal steroids such as beta-estradiol, effective derivatives or the like.

SUMMARY OF INVENTION

Provided by this invention is a transdermal dosage form which delivers transdermally an effective daily dose amount of one or more progestins (for example, progesterone, levonorgestrel, norethindrone or norethindrone acetate) and, optionally, also an effective amount of an estrogen steroid, preferably beta-estradiol.

The progestin transdermal forms of this invention are made using the following absorption enhancing composition:

a) an effective and biocompatible lower alkyl esterified polycarboxylic acid, said polycarboxylic acid selected from polycarboxylic acids having 3 to 12 carbon atoms;

b) an effective and biocompatible aliphatic monohydroxy alcohol, said aliphatic monohydroxy alcohol selected from aliphatic monohydroxy alcohols having 8 to 18 carbon atoms; and c) an effective and biocompatible diol selected from aliphatic diols having 3 to 6 carbon atoms.

An effective amount of progesterone or other progestin is added to the enhancing composition to form a homogeneous mixture, which can be converted to a gel by adding a gelling agent, preferably saturated or highly saturated with the selected progestin. The gelling agent selected is biocompatible, compatible with the progestin, the other components of the enhancing composition, and permits the progesterone or other progestin to be transdermally absorbed at an enhanced rate. The gelling agent has been found to be suitably polyvinylpyrrolidone, hydroxypropylmethyl cellulose, and the like. The gelled composition can be applied to the skin of a person needing progesterone or other progestin treatment in various dosage forms. It can be applied in measured quantity as a lotion or ointment. It can be suitably applied to a backing layer to make a dosage form which provides a suitable adhesive means to adhere the dosage form to the subject to be treated. For example, the backing layer can be shaped around the sides of the applied gelled progestin composition and then extended horizontally. To the underside of the thus formed peripheral ring can be applied a suitable adhesive layer for adhering the dosage unit to the skin of the subject to be treated. Also, instead of gelling agent or in addition to a gelling agent, the homogeneous mixture of progestin and enhancing composition can be added to an absorbent which is capable of absorbing the progestin. A suitable absorbent can be selected from an absorbent cotton, a biocompatible and suitable synthetic fibrous material including spun-bonded materials and other absorbents suggested to those skilled in the art. The final progestin-enhancing composition after addition of the gelling agent or absorbent will have a suitable viscosity for use in transdermal therapy.

The lower alkyl ester of polycarboxylic acid can suitably be a dialkyl citrate, for example, diethyl citrate. Other effective esters of polycarboxylic acids can be used which have a like effectiveness. Dialkyl tartrate can be selected.

The biocompatible aliphatic monohydroxy alcohol can be suitably lauryl alcohol. Other effective aliphatic monohydroxy alcohols can be used instead or in combination with lauryl alcohol. Suitably the monohydroxy alcohol has 10 to 12 carbon atoms.

The diol selected can be propylene glycol (1,2-propanediol). Other effective diols having 3 to 6 carbon atoms can be used instead of propylene glycol or in combination with propylene glycol. Other diols from which the diol used can be selected are 1,3-propanediol, 1,2-butanediol, 1,3-butanediol, 1,4-butanediol and the like or mixtures thereof. The diol selected desirably has 3 or 4 carbon atoms.

It has been found that the ratio of lower alkyl ester of polycarboxylic acid: aliphatic monohydroxy alcohol: aliphatic diol can be varied. It has been found that a ratio of 3:4:2 is suitable for progesterone and a presently preferred one if the respective components are diethyl citrate:lauryl alcohol:propylene glycol. The ratio used can vary substantially depending upon the enhancing composition components used, the progestin used, the estrogen used if utilized, the gelling agent, absorbent or other agent used. Generally speaking, if diethyl citrate, lauryl alcohol and propylene glycol are used as the three specified components, amounts of diethyl citrate, lauryl alcohol and propylene glycol are suitably selected based on 100 parts by weight of the three components from the following: 15–40 parts diethyl citrate, 10–60 parts lauryl alcohol, 10–60 parts propylene glycol.

Other suitable components within the respective definitions can be used instead of the three named components. The amount of the components can vary based upon the specific components selected, the progestin and optional estrogen selected, and other factors referred to above.

It is desired that the rate of absorption if progesterone is the selected progestin be a rate to provide an effective dosage, for example, 10–30 mg/day, usually about 20 mg is suitable. It is desired that in a desirably sized dosage unit, for example, about 5 to 30 cm$^2$, suitably about 20 cm$^2$, that the rate of absorption of progesterone be an effective amount in the range of about 10 mg to about 30 mg per day.

Alternatively, in place of the natural progestin, progesterone, one or more synthetic progestins can be used in an appropriate amount to provide the desired progestin activity. The synthetic progestin can be selected from those which are transdermally absorbable, biocompatible and effective. Illustrative synthetic progestins which can be used in the dosage forms of this invention can be selected from levonorgestrel, norethindrone, norgestimate, norethynodrel, dydrogesterone, ethynodiol acetate, hydroxyprogesterone caproate, medroxyprogesterone diacetate, norethindrone acetate, norgestrel, and the like and other effective progestins.

Also, instead of using a gelling agent to add to the enhancing composition containing progesterone or one or more other progestins as described above, the enhancing composition containing the progestin can be added to a biocompatible adhesive polymer which is compatible with the hormonal steroids present in the final dosage form and permits the hormonal steroids to be transdermally absorbed as desired. Various adhesive polymers can be used. Presently preferred adhesive polymers are acrylic adhesive polymers.

Another alternative is to absorb the progestins and the optional estrogen of the composition using a suitable biocompatible absorbent.

DETAILED DESCRIPTION OF THE INVENTION AND THE PREFERRED EMBODIMENTS

Figure 1:
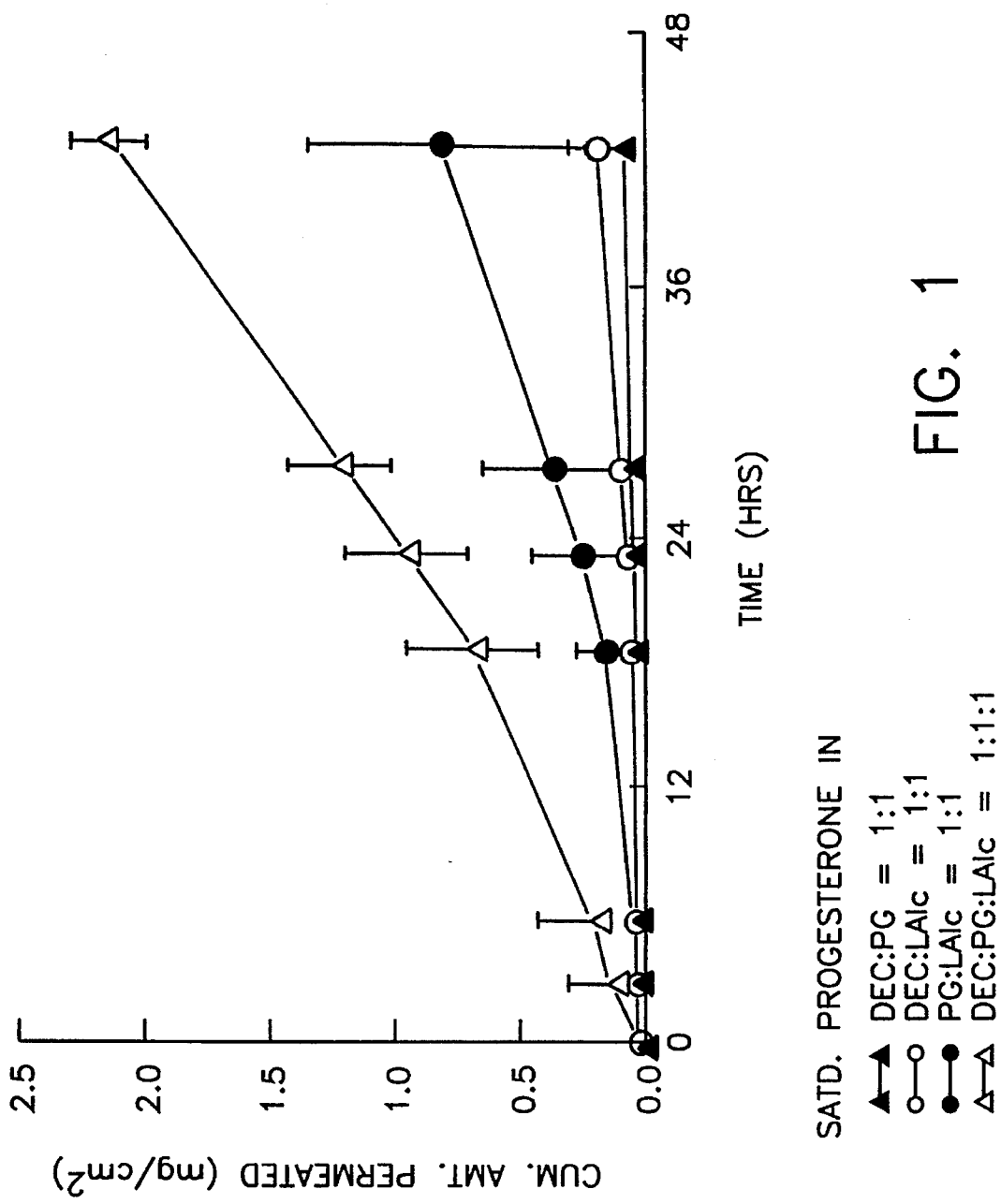
FIG. 1 is a graph showing in vitro skin permeation profiles of progesterone as taken from Table I. The graph is a plot of cumulative amounts of absorbed progesterone (mg/cm$^2$) vs. time (hours).
Figure 2:
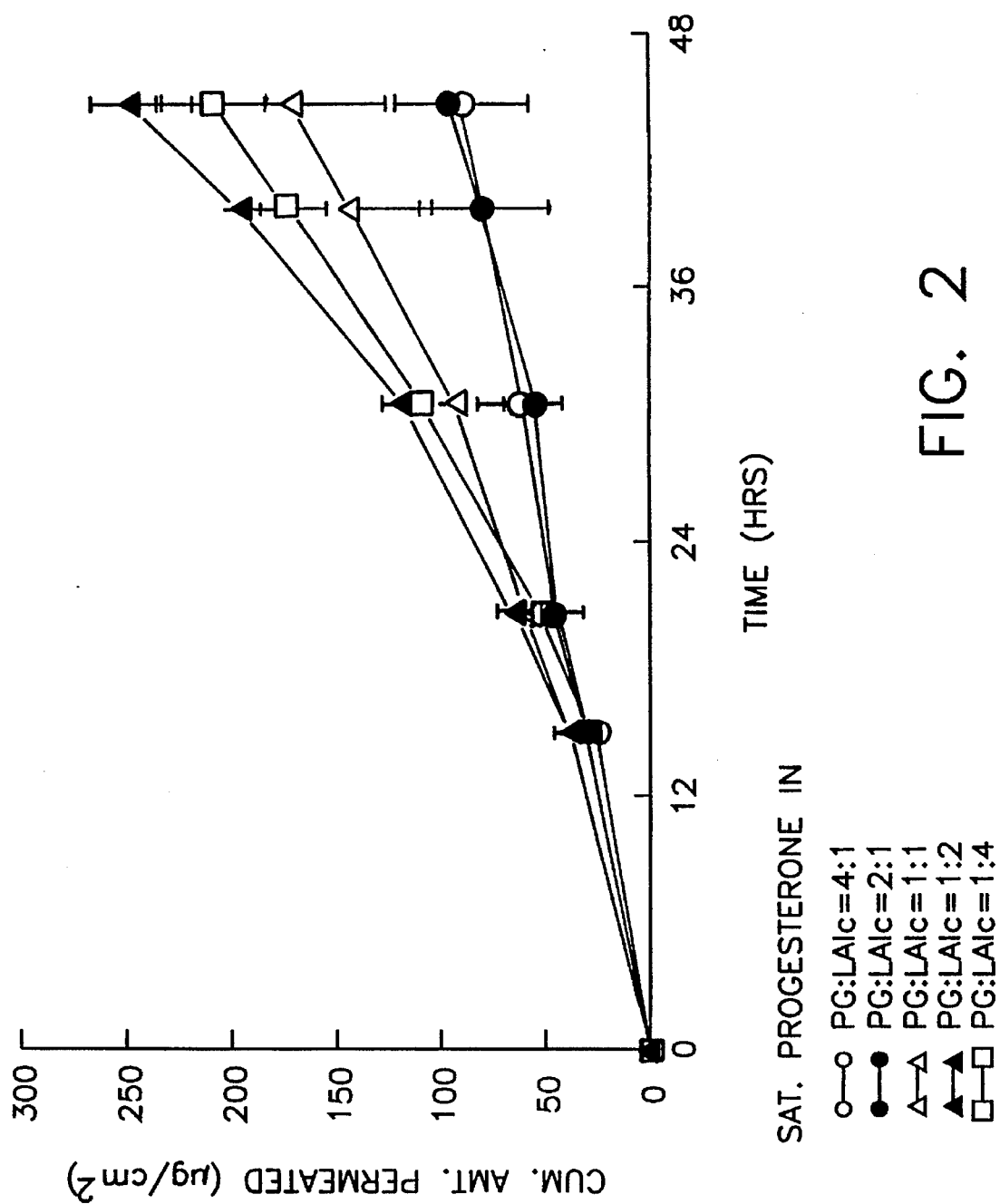
FIG. 2 is a graph showing in vitro skin permeation profiles of progesterone data as taken from Table 2. The graph is a plot of a cumulative amounts of transdermally absorbed progesterone (mg/cm$^2$) vs. time (hours).

In illustration of providing transdermal dosage units of this invention, absorption enhancing compositions are made to combine with progesterone or one or more other progestins and, optionally, with an estrogen.

A suitable amount of the lower alkyl esterified polycarboxylic acid such as 1–5 parts, suitably 3 parts, by weight is placed into a suitable container equipped with a mixing device. For this esterified polycarboxylic acid, it has been found suitable to employ a dialkyl ester of the six carbon polycarboxylic acid, citric acid, for example, diethyl citrate (DEC). A suitable amount of diethyl citrate is 3 parts. Also, a dialkyl ester of the four carbon polycarboxylic acid, tartaric acid, for example, diethyl tartrate, can be selected.

To the esterified polycarboxylic acid is added an amount of a biocompatible aliphatic monohydroxy alcohol. It has been found suitable to add about 4 parts by weight of the presently preferred aliphatic monohydroxy alcohol, lauryl alcohol (LA).

Then, an amount of a biocompatible diol which has 3 to 6 carbon atoms is added thereto. It has been found suitable to employ 2 parts by weight of propylene glycol (PG).

The combination of diethyl citrate, lauryl alcohol and propylene glycol can be stirred with heating to 35° to 40° C. For this purpose, a water bath can be used at such temperature of 35° to 40° C.

Then, to this transdermal absorption composition comprising diethyl citrate, lauryl alcohol and propylene glycol is added an effective amount of progesterone. It has been found that 10 percent (w/w) of progesterone is suitably added to the composition with stirring, until a homogeneous mixture is obtained.

If desired, an effective amount of 17-beta-estradiol or other estrogen compound can be added to the composition in order to provide an effective amount of an estrogen or to the adhesive of the peripheral ring of the final dosage unit. It is presently preferred to use 17-beta-estradiol. In the alternative, certain estradiol mono- and diesters can be employed which are biocompatible and which hydrolyze upon transdermal absorption to estradiol.

The amount of estradiol or other estrogen or combination of estrogens will be determined on the basis of the desired biological effect. If estradiol is utilized, an amount can be added to cooperate with the progesterone or other progestin component to provide the desired hormonal effect.

For example, an effective amount of an estrogen, desirably, estradiol, can be added to the enhancing transdermal absorption composition, such as an amount selected from about 0.25 to about 2 parts of estradiol per 10 parts of progesterone, assuming that progesterone is the progestin being utilized. The ratio of estradiol to progestin will be varied therefrom if a synthetic progestin is employed, depending on the relative potency of the synthetic progestin selected.

The combination of progestin and estrogen can be selected to provide a contraceptive or fertility control effect. The amount of each component for such fertility control will depend upon the respective progestin and estrogen components selected. It is highly desired that the dosage unit provide required daily dose amounts of progestin and estrogen for multiple days, desirably for 7 days.

At least one estrogen and at least one progestin as defined above are used, respectively. With the controlled release of the hormones at a relatively steady rate over a prolonged period, typically several days and preferably one week, the subject is provided with the benefit of a steady infusion of the hormones over a prolonged period.

One of the presently preferred estrogens is 17-beta-estradiol. It is a natural hormone and ordinarily transdermally delivered by an adaptable system of this invention at a desirable daily rate. The 17-beta-estradiol is compatible and can be used in the dosage unit. The transdermal dosage unit designed for one-week therapy is required to deliver at least about 100 to about 500 mcg (preferably about 125 to about 250 mcg)/day of norgestimate, about 1000 mcg (preferably about 500 to about 1500 mcg)/day of norethindrone or about 25 to about 200 mcg (preferably about 50 to about 150 mcg)/day of levonorgestrel and 20–50 mcg/day of 17-beta-estradiol (or an equivalent effective amount of ethinyl estradiol or another estrogen). In fertility control, that amount of progestin is believed to be necessary to inhibit ovulation and that amount of estrogen is believed needed to maintain normal female physiology and characteristics. Derivatives of 17-beta-estradiol which are biocompatible, capable of being absorbed transdermally and preferably bioconvertible to 17-beta-estradiol can also be used, if the amount of absorption meets the required daily dose of the estrogen component and if the hormone components are compatible. Such derivatives of estradiol can be selected from esters, either mono-or di-esters. The mono-esters can be either 3- or 17- esters. The estradiol esters can be, illustratively speaking, estradiol-3, 17-diacetate; estradiol-3-acetate; estradiol-17-acetate; estradiol-3,17-divalerate; estradiol-3-valerate; estradiol-17-valerate; 3-mono, 17-mono and 3,17-dipivilate esters; 3-mono, 17-mono and 3,17-dipropionate esters; corresponding cypionate, heptanoate, benzoate and the like esters; ethinyl estradiol; estrone; and other estrogenic steroids and derivatives thereof which are transdermally absorbable, including benzestrol, chlorotrianisene, dienestrol, mestranol, and the like.

The progestin can be selected from norethindrone, norgestimate, levonorgestrel (or norgestrel containing both levonorgestrel and its (+) enantiomer), norethynodrel, dydrogesterone, ethylnodiol diacetate, hydroxyprogesterone caproate, medroxyprogesterone acetate, norethindrone acetate, norgestrel, progesterone, and the like.

If levonorgestrel is used as the progestin, account must be taken of its high progestin potency on a weight basis. The amount used adequate for a daily use can vary so long as it is effective in combination with the estrogen used to provide the desired fertility control or estrogen replacement. Ordinarily, in fertility control, an effective amount in the range from about 25 to about 200 mcg will be used, preferably about 50 to about 150 mcg per dosage unit. In making an estrogen replacement dosage unit, lower daily dosages are adequate for effective estrogen therapy.

It will be suggested to those skilled in the art to use other estrogens or progestins in forming the dosage units of this invention. Such use of other estrogens and progestins are intended to be within the scope of this invention insofar as use thereof provides satisfactory dosage units within the spirit of this invention.

It is further desirable to vary the ratio of progestin/estrogen absorption dosage rate among the first, second and third week dosage units.

In the first week dosage unit, it is desirable to have a rate of absorption of about equal amounts of progestin and estrogen (ratio of about 1/1), based upon use of levonorgestrel as the progestin and estradiol as the estrogen. The ratio can be varied such as from about 0.75:1 to about 1.25:1 to provide an effective dosage amount. In use of other progestins and estrogen, the amounts used will be adjusted to provide a rate amounts absorbed which are bioequivalent to the respective rate amounts of progestin and estradiol.

In the second week dosage unit, a progestin/estrogen rate of absorption ratio of about 1.5:1 is, generally speaking, suitable. However, the rate of absorption ratio can be varied such as from 1.25:1 to about 2.5:1, depending upon several factors encountered in treatment.

In the third week dosage unit, a rate amount of absorption ratio of about 2.5:1 progestin to estrogen, based again upon use of levonorgestrel and estradiol, is, generally speaking, suitable. The rate ratio can be varied to provide the effective dosage amount, for example, from about 2:1 to about 4:1 or 5:1, depending upon variables encountered in practice, to provide a safe and effective fertility control. Again, in the use of other progestins and estrogens other than levonorgestrel and estradiol, adjustments to provide rate amounts bioequivalent to levonorgestrel and estradiol, respectively, will be made.

In the use of synthetic estrogens, it is ordinarily advised presently to keep daily administration below about 50 mcg per subject.

In estrogen replacement therapy, it is ordinarily advised that estradiol administration can range up to about 150 mcg per subject per day.

The progesterone-containing composition can be converted to a gel for purposes of forming a suitable transdermal absorption form. For this purpose, a biocompatible gelling agent is employed which is also compatible with the components of the progesterone-containing transdermal absorption composition. The gelling agent must also permit or not interfere with the transdermal absorption of progesterone and estrogen component, if the estrogen component is employed. A gelling agent which provides such characteristics and which provides a suitable consistency in the final gel form can be used. It has been found that polyvinylpyrrolidone ("PVP") with various average molecular weights is a presently preferred gelling agent. A suitable average molecular weight of polyvinylpyrrolidone is 360,000.

Also it has been found suitable to use hydroxypropylmethyl cellulose ("HPMC").

Forming the gel composition, a suitable amount of the gelling agent is slowly added to the progesterone-containing transdermal absorption composition with stirring and maintaining the composition at an elevated temperature such as 37° C. The quantity and properties of the selected gelling agent will depend on the consistency desired of the final gelled composition, the transdermal absorption rate desired and other characteristics of the gelled form. It has been found in using a suitable polyvinylpyrrolidone that quantities such as 1, 2, 4 or 8% can be used to provide usable and preferred gel compositions. The use of hydroxypropylmethyl cellulose as the gelling agent, likewise various quantities of hydroxypropylmethyl cellulose, can be used, depending on the desired viscosity of the final gel form of the composition. It has been found suitable to use an amount selected from 1, 2 or 3 or the like amounts.

Upon completion of the addition of the gelling agent to the progesterone-containing composition, the stirring can be continued at elevated temperature until the mixture of transdermal absorption composition containing progesterone and the gelling agent becomes homogeneous. A mixture is then cooled as, for example, to room temperature. The cooled gelled composition then can be shaped into suitable configurations for actual use by subjects desiring the progesterone treatment. In the alternative, the gelled composition can be added to suitable forms or mold configurations to provide upon cooling a solidified gel form which can be used in final transdermal absorption administration of the progesterone-containing composition. The final gelled form of the progesterone-containing composition will be selected on the bases of the desired form of administration, convenience of administration, and the like. For example, the composition can be applied in measured amounts as an ointment or a lotion for transdermal administration.

Also, the gelled composition (or the absorbents containing progesterone composition) can be transferred to a premolded cavity comprising a backing layer which is substantially impervious to the components of the progesterone-containing composition. Suitable backing materials are available for use from commercial sources such as a composite backing layer sold under the designation Scotch Pak 1109, by 3M Company. The composition can be applied to the backing in a conventional manner. It is suitable to provide suitable length and width of a molded backing layer and apply thereto the amount of the gelled form of the progesterone-containing composition. The gelled form can be surrounded or enclosed on the sides thereof by the backing layer by forming the backing layer around the sides of the progesterone-containing form to overlay the side or sides of the progesterone-containing form and then extend outwardly in a manner that the surface of the extension of the backing layer can be a base for an adhesive to hold the dosage unit in intimate contact with subjects being treated with the progesterone.

A suitable material or adhesive for this purpose can be selected from those currently available, such as polyacrylic adhesive or certain biocompatible silicone or polyisobutylene adhesives or the like. After the dosage unit with the overlaid backing is completed, the adhesive means and the gelled form then are finally covered in conventional therapeutic practice with a releasable protective film layer which is made from materials which are substantially impermeable to the pharmaceutical, the transdermal absorption enhancing agent and any other components of the dosage unit. The polymer materials and metal foil laminates used for the backing layer can be used to make the protective layer, provided the layer is made strippable or releasable such as by applying conventional siliconizing. A suitable releasable material for use with silicone polymer adhesive is Scotch Pak 1022 material sold by the 3M Company or BioRelease material sold by Dow Corning.

Alternatively, the progestin-composition can be added with mixing to certain polymers or adhesives to form a dosage form rather than using a gelling agent or absorbent. It will be apparent to those skilled in the art that certain adhesive compositions be employed for purposes of containing or increasing the viscosity of the progesterone-containing composition. For example, compatible adhesives such as polyacrylics, polyisobutylene, or polysilicone adhesives can be employed so long as progesterone or other progestin and any other hormones present such as an estrogen, for example, estradiol, are biocompatible and will be transdermally absorbed from the dosage unit into the skin and into the system of the subject desiring the steroid hormonal treatment.

In making the dosage units using the adhesive compositions which provide the desired synthetic progestins or other hormonal absorption, the composition containing the hormonal steroids can be readily coated onto an impermeable backing layer, such as a composite sold under the designation Scotch Pak 1109 by 3M Company. Coating equipment can be used to coat the backing layer to a desired thickness. A coater which can be used is a Warner-Mathis laboratory coater, type LTSD with built-in laboratory dryer LDF. Thickness of the hormonal steroid adhesive layer can be accurately controlled to desired thickness, such as to 400 microns (wet), using such a designed coater-dryer.

The amount of hormonal steroid added to the adhesive solution used for coating can vary so long as there is provided an effective amount for transdermal absorption. Ordinarily, it has been found that about a 5–30 percent amount of synthetic progestins based upon the total weight of the adhesive coating mixture provides an effective amount of transdermal absorption. The amount of synthetic progestins or other hormonal steroid used can be varied depending upon the rate of absorption desired and the particular adhesive or polymer used in making the dosage unit. The effective amount can be selected from a range of from about 5 to about 30 percent based upon the weight of the coating mixture used to make the dosage unit, a more preferable range being from about 8 to about 25 percent, based on said weight. The amount of the enhancing composition and the ratio of the components thereof can also be varied so long as an effective amount of progesterone or other steroid hormone transdermal absorption is provided.

Progestins administered to the subject being treated can vary depending upon the desired treatment factors. It has been found suitable depending upon the patient indications to administer an amount in the range of about 10 to 30 mg of progesterone per day. The dosage unit must be so constituted as to permit such administration on a daily basis.

The size of the dosage unit varies depending upon the concentration of the progestin and other factors. It has been found suitable to use a dosage unit which has a surface area 5 to 50 $cm^2$. A surface area of about 20 $cm^2$ is ordinarily suitable area of transdermal absorption surface.

The role of estradiol or other estrogen used is to reduce customary menopausal symptoms, cyclic hot flashes and other common symptoms.

Instead of progesterone, as mentioned above, a synthetic progestin can be used alone or in combination with each other. The synthetic progestin can be selected from norethindrone, norgestimate, levonorgestrel, norethynodrel, dydrogesterone, ethynodiol acetate, hydroxyprogesterone caproate, medroxyprogesterone diacetate, norethindrone acetate, norgestrel, progesterone, and the like.

As referred to above, the presently preferred estrogen is 17-beta-estradiol. It is a natural hormone and ordinarily transdermally delivered by an adaptable system of this invention at a desirable daily rate. Derivatives of 17-beta-estradiol which are biocompatible, capable of being absorbed transdermally and preferably bioconvertible to 17-beta-estradiol can also be used, if the amount of absorption meets the required daily dose of the estrogen component and if the hormone components are compatible. Such derivatives of estradiol can be selected from esters, either mono-or diesters, as described above. Other estrogens can be used as described above.

The hormonal steroid compositions of this invention, as well as the transdermal compositions of this invention which are used in making the hormonal steroid compositions and dosage units can contain certain other components, certain stabilizers, antioxidant agents and the like which are known to the art for use in such compositions.

The compositions of this invention can be evaluated for their effectiveness in delivering the desired amount of progesterone and other hormones which might be present by the following procedure. The dosage units are evaluated by using a skin specimen of human cadaver by the procedures described by Y. W. Chien, K. Valia and U. V. Doshin, Drug Develop. & Ind. Pharm., 11(7), 1195–12 (1985).

The transdermal evaluation of progesterone or other progestin and estrogen steroids present in the composition of the invention, permeation flux is measured at 37° C. 3.5 ml of the composition containing steroid is used as the pharmaceutical reservoir; 3.5 ml of 40% polyethylene glycol (PEG-400) solution as the receptor vehicle. The evaluation shows the cumulative amount of steroid such as progesterone which is absorbed (mg/cm$^2$) vs. time (hours).

The following examples are in illustration of the invention and are not intended to be limited. To those skilled in the art when reading this specification, modifications will be suggested to the invention as disclosed herein. Those modifications which are within the spirit of this invention are intended to be within the scope thereof.

EXAMPLE 1

A composition for making progesterone transdermal absorption composition is prepared by adding the following to a flask with mixing by Vortex at room temperature:

1) 3 parts by weight diethyl citrate (15 g)
2) 4 parts by weight of lauryl alcohol (20 g)
3) 2 parts by weight of propylene glycol (10 g)

Place the flask containing the transdermal absorption composition into a water bath and heat with stirring to 37° C. Then, add to the composition, 4.5 g of progesterone and mix well by Vortex.

EXAMPLE 2

To the progesterone-containing composition of Example 1, are added with stirring differing quantities of polyvinylpyrrolidone ("PVP", 1%, 2%, 4% or 8%) or hydroxypropylmethyl cellulose ("HPMC", 1%, 2% or 3%) on a weight/weight basis. The stirring is continued until the mixture becomes homogeneous. The mixtures then are cooled to room temperature.

The gelled composition can be applied in measured amount to the skin of human needing progesterone treatment.

A suitably formed amount of the gelled compositions are placed into a premolded cavity of backing layer which is substantially impervious to the ingredients of the gelled compositions. Polyvinylpyrrolidone has been found to be suitable for this use. The surface area of the gelled forms are 20 cm$^2$. The backing layer is cut to a suitable length and shaped around the sides of the shaped form of the composition and then is extended in a horizontal direction to form a peripheral ring essentially planar with the surface of the formed composition. On the surface of the thus formed peripheral ring is placed a suitable adhesive containing estradiol such as a biocompatible polyacrylic adhesive.

The above experiment can be repeated by adding a suitable absorbent to the composition composing hormonal steroid and enhancing composition to provide a consistency suitable to place into the pre-molded cavity of the impervious backing layer.

EXAMPLE 3

These experiments are carried out using the enhancing composition having a lower alkyl esterified polycarboxylic acid (such as diethyl citrate), a compatible aliphatic monohydroxy alcohol (such as lauryl alcohol) and a biocompatible diol selected from polyalcohols having 3 to 6 carbon atoms (such as propylene glycol).

The following table shows skin permeation fluxes of progesterone from formulations via a combination of two or three of the above components.

TABLE 1

| Progesterone Skin Fluxes from Formulations | |
|---|---|
| Ratio of Formulation Ingredients (DEC:LA:PG) | Progesterone Skin Flux [mcg/cm$^2$/hr (SD)] |
| 1:0:1 | 2.32 (0.57) |
| 1:1:0 | 6.62 (1.17) |
| 0:1:1 | 28.62 (14.77) |
| 1:1:1 | 61.58 (13.12) |

The following experiments were carried out to show the optimization of lauryl alcohol and propylene glycol. Various formulations of saturated progesterone in solutions with increasing ratio of lauryl alcohol to propylene glycol are prepared. The progesterone fluxes were calculated and tabulated as shown in the following Table 2.

TABLE 2

| Progesterone Skin Fluxes from Formulations With Varied Ratios of LA and PG | |
|---|---|
| Ratio of PG:LA | Progesterone Skin Flux [mcg/cm$^2$/hr (SD)] |
| 4:1 | 2.03 (0.64) |
| 2:1 | 2.83 (0.34) |
| 1:1 | 5.52 (1.31) |
| 1:2 | 9.18 (0.56) |
| 1:4 | 7.10 (0.99) |

The following experiments were carried out as shown in Table 3. The above data show that the maximum progesterone flux is achieved when the ratio of lauryl alcohol to propylene glycol equals 2:1.

FIG. 1 shows a typical skin permeation profile of progesterone.

Figure 3:
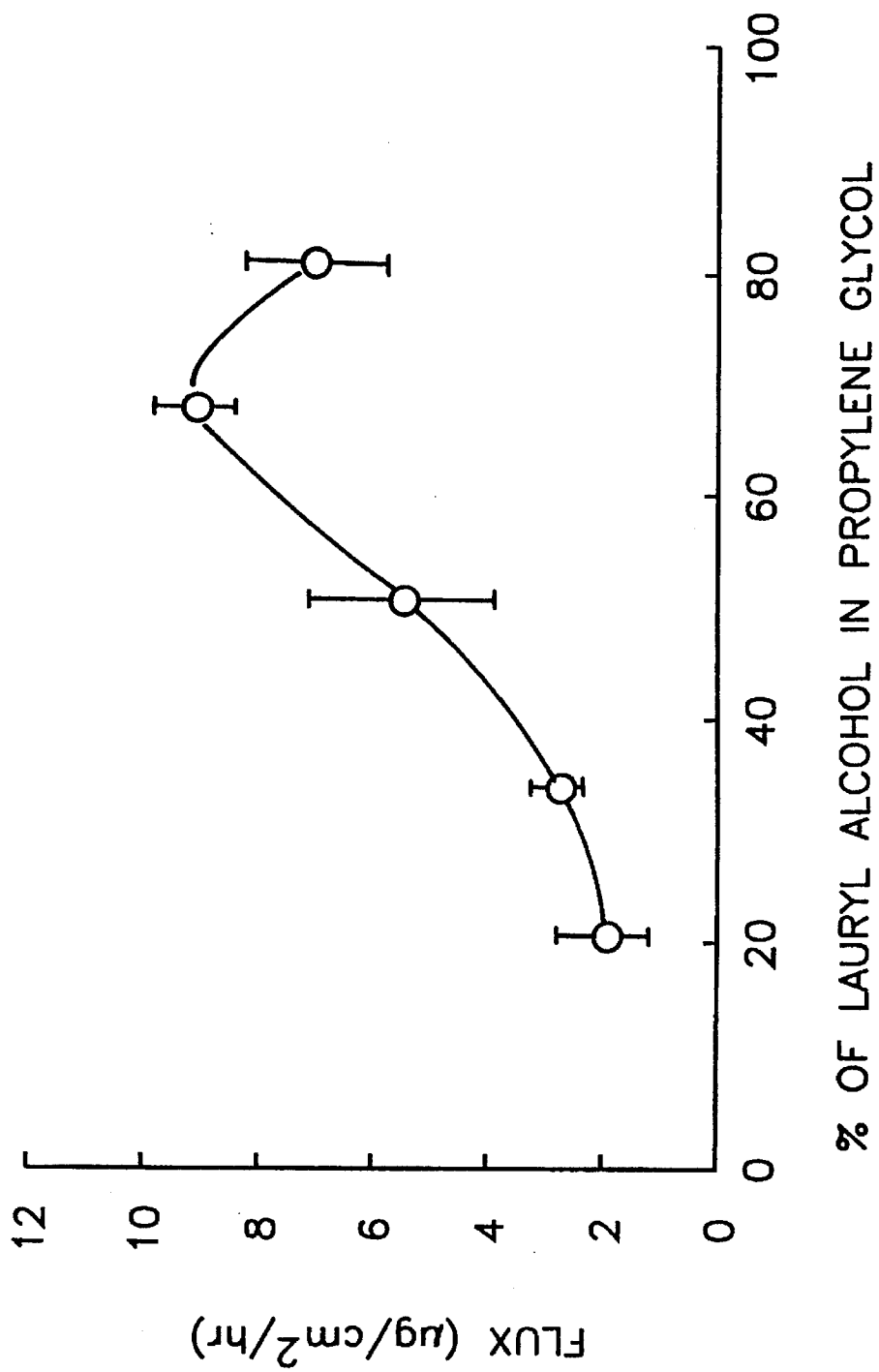
FIG. 3 corresponds to the data of Table 2 and shows effect of lauryl alcohol loadings in propylene glycol on skin flux of progesterone. The data is a plot of the flux of progesterone (mg/cm$^2$/hr) vs. percent lauryl alcohol in propylene glycol.
Figure 4:
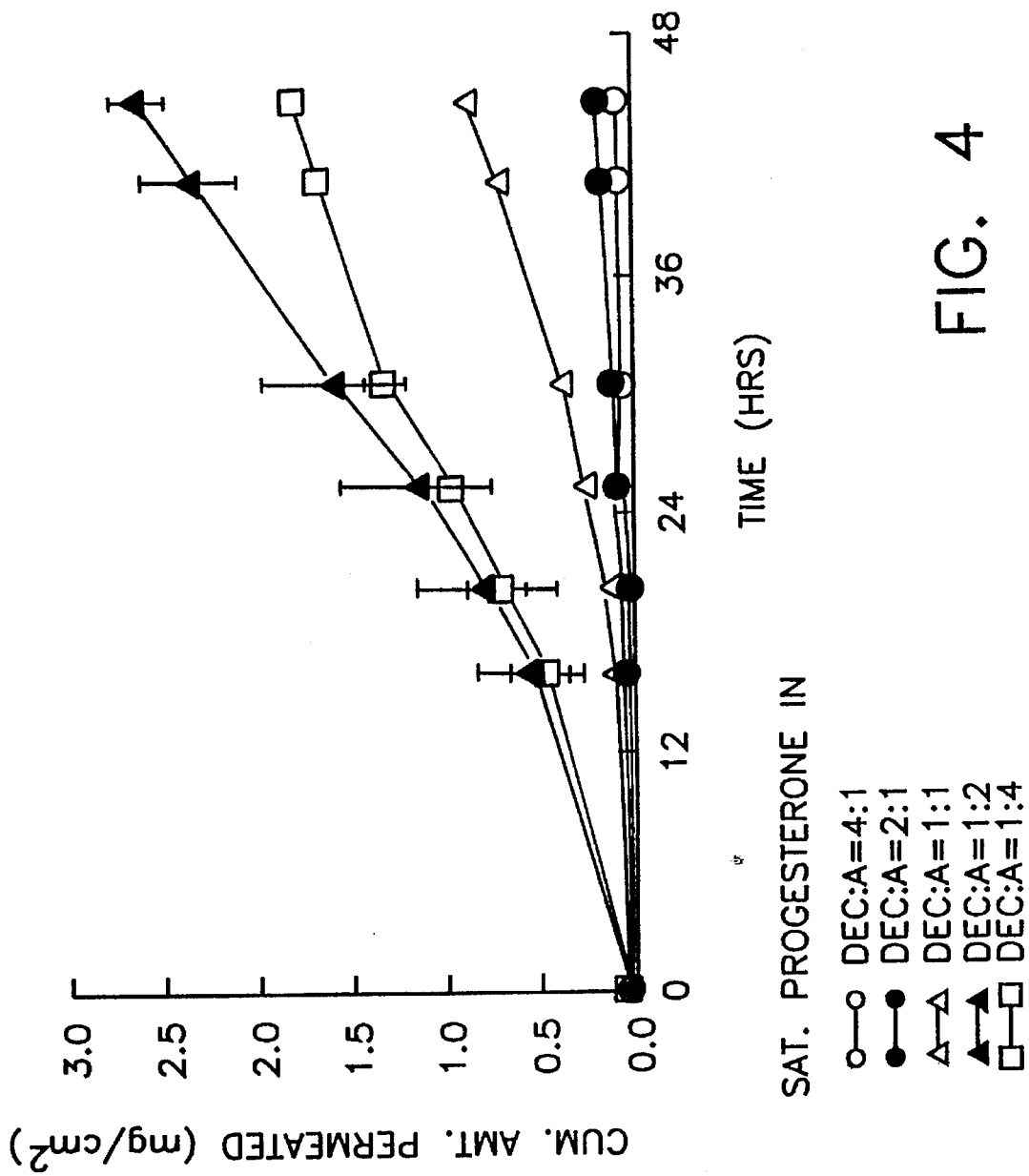
FIG. 4 is a graph showing in vitro skin permeation profiles of progesterone as taken from Table 3. The graph is a plot of the cumulative amount of transdermally absorbed progesterone (mg/cm$^2$) vs. time (hours).
Figure 5:
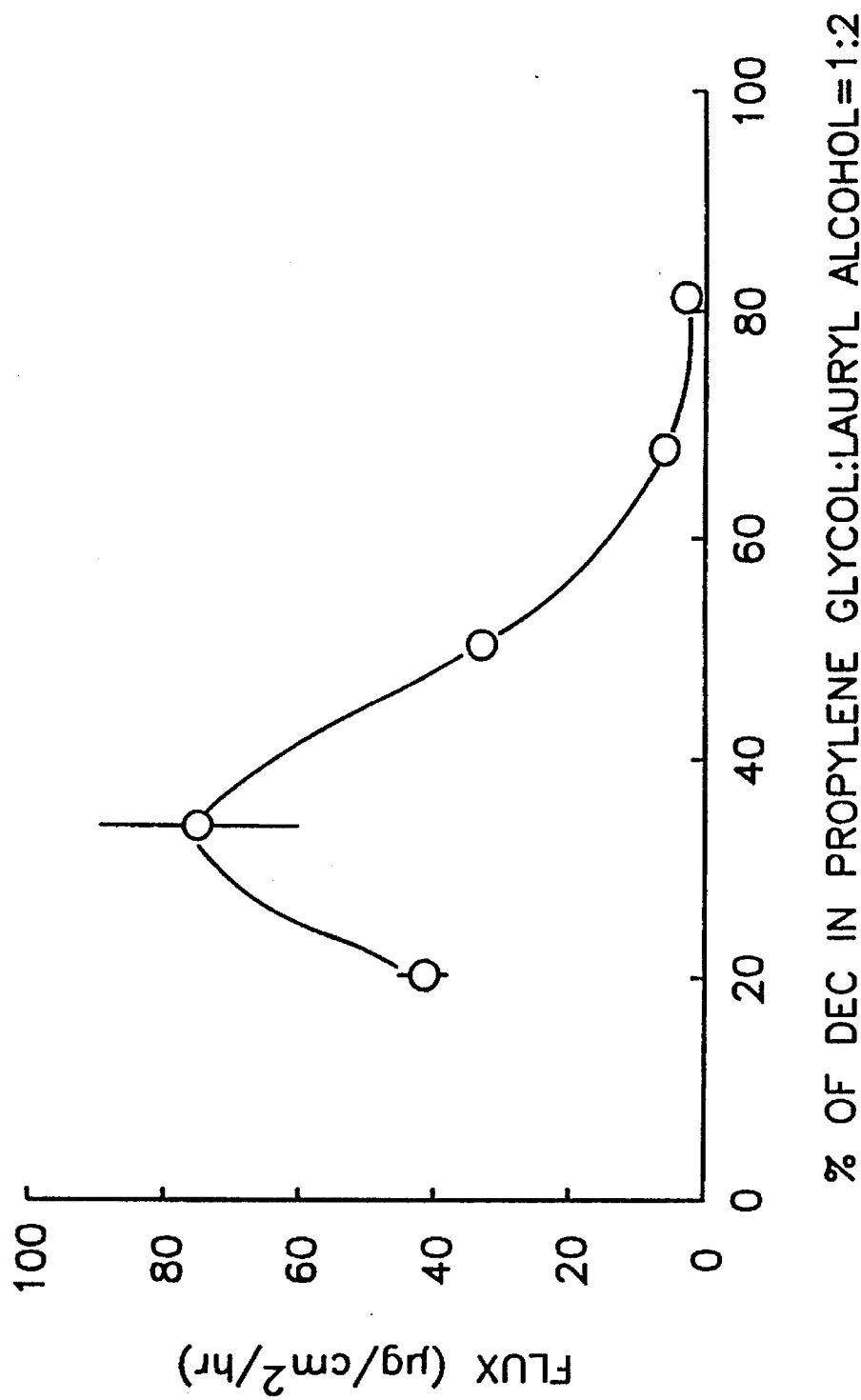
FIG. 5 is a graph showing the effect of diethyl citrate loadings in propylene glycol:lauryl alcohol (ratios 1:2) on skin flux of progesterone as taken from Table 3. The graph is a plot of the flux (mcg/cm$^2$/hour) vs. percentage of diethyl citrate in propylene glycol:lauryl alcohol (ratio 1:2).
Figure 6:
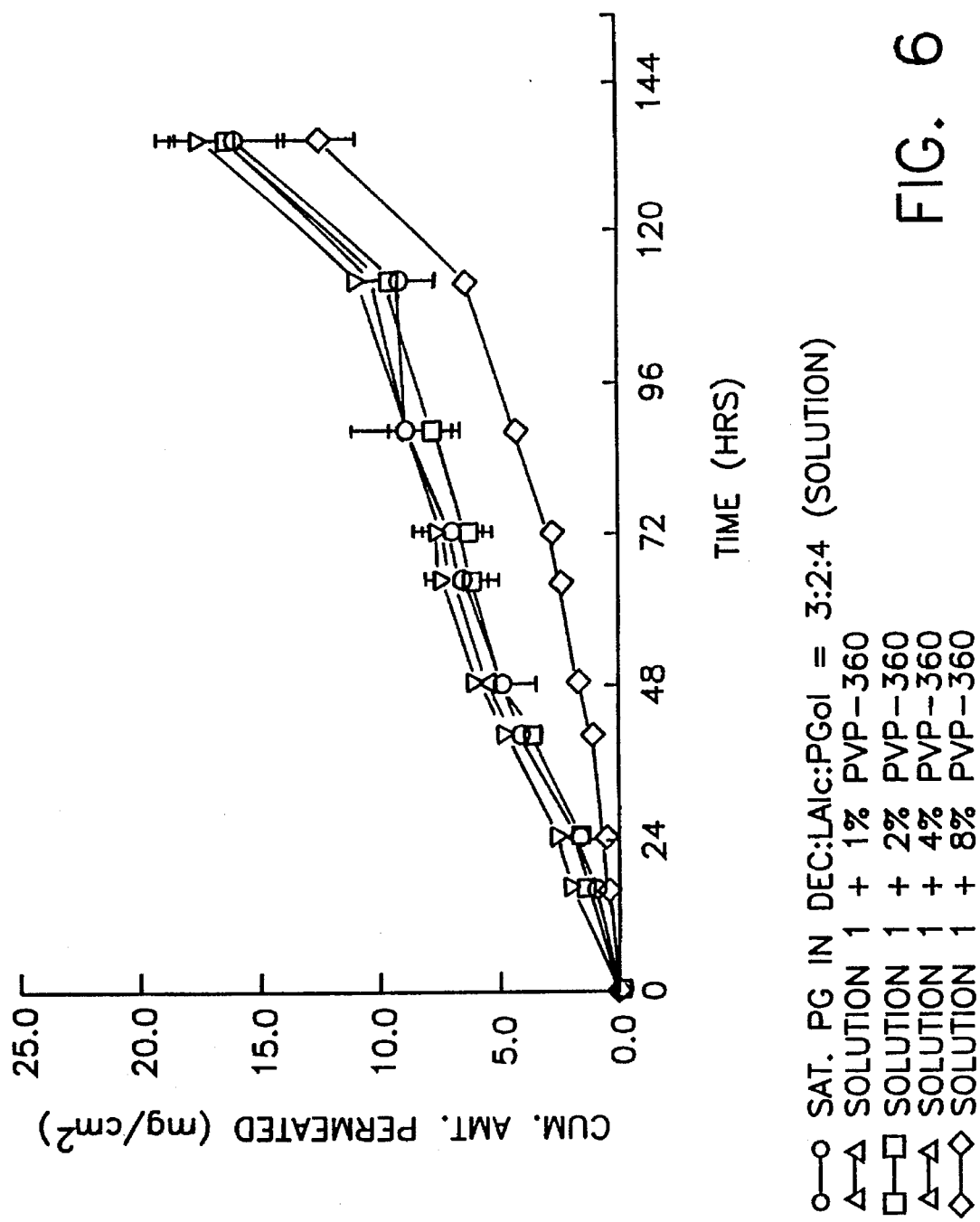
FIG. 6 is a graph showing the effect of concentrations of gelling agent on in vitro skin permeation fluxes of progesterone as taken from Table 4. The graph is a plot of the cumulative amount of transdermally absorbed progesterone (mg/cm$^2$) vs. time (hours).
Figure 7:
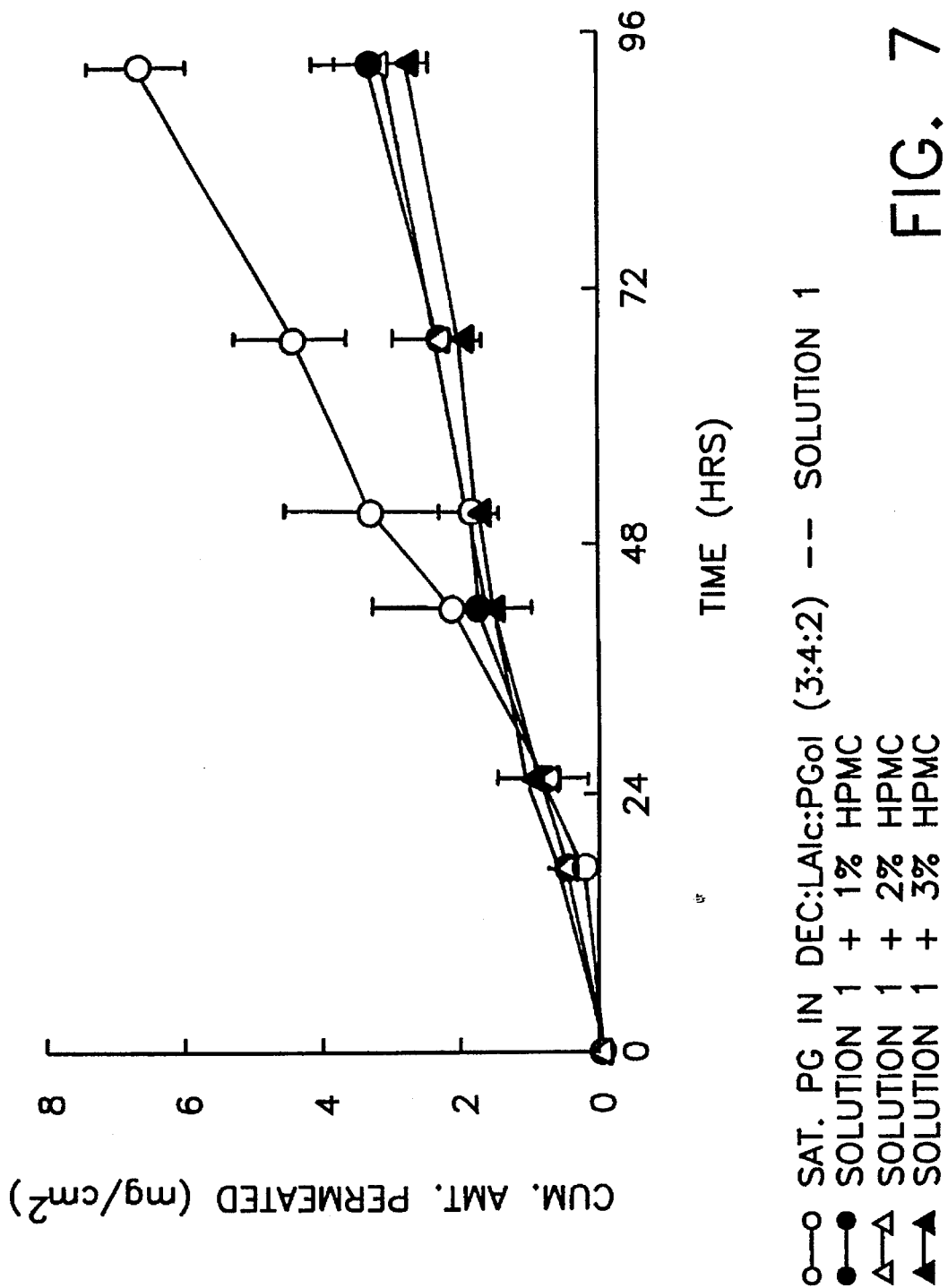
FIG. 7 is a graph showing the effect of HPMC loadings on progesterone skin flux as taken from Table 5. The graph is a plot of the cumulative amount of transdermally absorbed progesterone (mg/cm$^2$) vs. time (hours).

The following experiments are carried out using a lauryl alcohol:propylene glycol ratio of 2:1. Experimentation is carried out to utilize varying amounts of diethyl citrate. Formulations of progesterone skin fluxes are listed in Table 3 provided hereby. The progesterone skin fluxes vs. the percentages of diethyl citrate due to the 2:1 ratio of lauryl alcohol:propylene glycol are shown in FIG. 3. The data shows that 3:4:2 ratio of diethyl citrate:lauryl alcohol:propylene glycol is an optimal ratio to deliver progesterone.

TABLE 3

Progesterone Skin Fluxes From Formulations with DEC, LA and PG

| Ratio of DEC:LA:PG = 2:1 | Progesterone Skin Flux [mcg/cm²/hr (SD)] |
|---|---|
| 4:1 | 2.55 (0.93) |
| 2:1 | 5.82 (0.30) |
| 1:1 | 32.22 (26.13) |
| 1:2 | 73.79 (11.60) |
| 1:4 | 41.35 (2.32) |

The following experimentation is carried out to show the effect of loading amounts of gelling agent to provide a variation of viscosity of an optimized formulation in which the amount of skin flux of progesterone would not be unduly interfered with the amount of PVP-360 and HPMC with the above 3:4:2 ratio composition. The following table shows the results of the experimentation wherein differing amounts of PVP-360 are added. Four percent or less PVP does not diminish greatly the amount of progesterone absorbed. It is noted that PVP-360 does significantly reduce the amount of skin flux of progesterone, the reduction being 40–50% as shown by the data of Table 4.

The following Table 4 experimentation carried out for PVP-360 is repeated utilizing differing concentrations of HPMC wherein the effect of HPMC of concentrations on progesterone flux shows that the amount of progesterone skin flux from the formulations utilizing HPMC as the gelling agent was about one-third of the control utilizing no HPMC. There was not a large reduction of progesterone skin flux once the amount of HPMC gelling agent concentration was increased from the original 1 percent by weight. The data is shown on the following Table 5.

TABLE 4

The Effect of PVP-360 on Progesterone Skin Flux

| PVP-360 Loadings | Progesterone Skin Flux [mcg/cm²/hr (SD)] |
|---|---|
| 0 | 88.9 (17.9) |
| 1 | 94.7 (8.4) |
| 2 | 86.9 (11.0) |
| 4 | 78.6 (25.9) |
| 8 | 49.3 (6.4) |

TABLE 5

The Effect of HPMC on Progesterone Skin Flux

| HPMC Loadings (%, w/w) | Progesterone Skin Flux [mcg/cm²/hr (SD)] |
|---|---|
| 0 | 75.1 (14.8) |
| 1 | 29.9 (8.2) |
| 2 | 28.5 (7.0) |
| 3 | 21.0 (5.0) |

EXAMPLE 4

The following is the effect of percentage of the enhancing composition on NE or NA flux.

| Formulation | Mixture DEC:LA:PGol = 3:4:2 | Skin Flux (mcg/cm²/hr) NE (SD) | NA (SD) |
|---|---|---|---|
| NE-P1 | 18 | 1.20 (0.10) | 1.44 (0.44) |
| NE-P2 | 15 | 1.20 (0.23) | 1.21 (0.18) |
| NE-P3 | 10 | 0.79 (0.11) | 0.74 (0.11) |

NE: Norethindrone
NA: Norethindrone Acetate

EXAMPLE 5

The following shows the effect of aliphatic alcohol on progesterone flux:

Progesterone Skin Fluxes

| P4 in Mixture | Progesterone Skin Flux [mcg/cm²/hr (SD)] |
|---|---|
| DEC:LA:PG = 3:4:2 | 64.07 (19.62) |
| DEC:EtOH:PG = 3:4:2 | 3.79 (1.75) |

EtOH: Ethanol

EXAMPLE 6

The following tables show flux data for estradiol and levonorgestrel.

Estradiol Fluxes from Formulations

| Ratio of Formulation Ingredients (DEC:PG:LA) | Estradiol Skin Flux [mcg/cm²/hr (SD)] |
|---|---|
| 3:4:2 | 0.245 (0.086) |
| 0:4:2 | 0.092 (0.007) |
| 0:0:0 | 0.063 (0.011) |

Levonorgestrel Fluxes from Formulations

| Ratio of Formulation Ingredients (DEC:PG:LA) | Levonorgestrel Skin Flux [mcg/cm²/hr (SD)] |
|---|---|
| 3:4:2 | 0.309 (0.118) |
| 0:4:2 | 0.128 (0.011) |
| 0:0:0 | 0.070 (0.020) |

What is claimed is:

1. A composition useful for providing enhanced transdermal absorption of progesterone, synthetic progestins and estrogens, comprising in combination the following components:

a) an effective and biocompatible lower dialkyl ester of citric acid;

b) a monohydroxy alcohol selected from the group consisting of decyl alcohol and lauryl alcohol; and c) propylene glycol as a diol component.

2. A composition of claim 1 wherein the lower alkyl ester used is diethyl citrate, the monohydroxyl alcohol used is lauryl alcohol and the diol used is propylene alcohol.

3. A composition of claim 1 wherein the composition has per hundred parts by weight of the composition, the following:

a) 15–40 parts of the lower alkyl ester of citric acid;

b) 10–60 parts of the monohydroxy alcohol component; and c) 10–60 parts of propylene glycol.

4. A composition of claim 3 wherein the components a, b and c are respectively, diethyl citrate, lauryl alcohol and propylene glycol.

5. A composition of claim 4 wherein the ratio of said components is about 3:4:2 or about 3:2:4.

6. A transdermal dosage form comprising a composition having the following components:

1) an effective amount of a progestin to provide a transdermal daily dose amount thereof and optionally an effective amount of an estrogen to provide a transdermal daily dose amount thereof; and 2) an effective amount of a transdermal absorption enhancing composition which enhances the transdermal absorption of said progestin comprising in combination the following:

a) effective amount of a biocompatible lower alkyl ester of citric acid;

b) effective amount of a monohydroxy alcohol selected from the group consisting of decyl alcohol and lauryl alcohol; and c) effective amount of propylene glycol.

7. A dosage form of claim 6 wherein said composition has present an effective amount of beta-estradiol or other estrogen or combination thereof.

8. A dosage form of claim 6 wherein the composition for providing enhanced absorption uses a lower alkyl ester of citric acid.

9. A dosage form of claim 6 wherein the composition for providing enhanced absorption uses a monohydroxy alcohol selected from the group consisting of decyl alcohol and lauryl alcohol.

10. A dosage form of claim 6 wherein the composition for providing enhanced absorption uses propylene glycol as a diol.

11. A dosage form of claim 6 wherein the composition for providing enhanced absorption uses a diethyl citrate, decyl or lauryl alcohol, and propylene glycol.

12. A dosage form of claim 6 wherein the composition for providing enhanced absorption uses per hundred parts by weight of the composition, the following:

a) 15–40 parts of the lower alkyl ester of citric acid;

b) 10–60 parts of the monohydroxyl alcohol component; and c) 10–60 parts of propylene glycol.

13. A dosage form of claim 12 wherein the composition for providing enhanced absorption wherein the components a, b and c are respectively, diethyl citrate, lauryl alcohol and propylene glycol.

14. A dosage form of claim 13 wherein the ratio of said components is about 3:4:2 or about 3:2:4.

15. A dosage form of claim 6 which is adapted for contraceptive use.

16. A dosage form of claim 6 which is adapted for hormone replacement use.

17. A dosage form of claim 6 wherein said composition is applied to an impervious backing layer.

18. A dosage form of claim 17 wherein the composition is in the form of a gel.

19. A dosage form of claim 18 wherein the progestin is progesterone.

20. A dosage form of claim 17 wherein the composition applied to the backing layer is dispersed in a biocompatible adhesive.

21. A process of transdermally administering a progestin and optionally also an estrogen using a dosage form selected from those described in claims 6, 7, 8, 9, 10, 11, 12, 13, 14, 15, 16, 17, 18, 19 or 20.

* * * * *